(12) United States Patent
Shalaby et al.

(10) Patent No.: US 8,298,260 B2
(45) Date of Patent: Oct. 30, 2012

(54) COMPLIANT, LONG-LASTING ABSORBABLE MONOFILAMENT SUTURES

(75) Inventors: Shalaby W Shalaby, Anderson, SC (US); James M Lindsey, III, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 1322 days.

(21) Appl. No.: 11/596,547

(22) PCT Filed: Nov. 29, 2005

(86) PCT No.: PCT/US2005/042978
§ 371 (c)(1),
(2), (4) Date: Nov. 15, 2006

(87) PCT Pub. No.: WO2006/058305
PCT Pub. Date: Jun. 1, 2006

(65) Prior Publication Data
US 2008/0058870 A1    Mar. 6, 2008

(51) Int. Cl.
*A61B 17/04*    (2006.01)

(52) U.S. Cl. ........................................ 606/230
(58) Field of Classification Search .................. 606/228, 606/230, 229, 231; 424/443, 444; 427/2.31
See application file for complete search history.

(56) References Cited

U.S. PATENT DOCUMENTS

| | | | | |
|---|---|---|---|---|
| 4,052,988 A | * | 10/1977 | Doddi et al. | 606/231 |
| 4,994,074 A | * | 2/1991 | Bezwada et al. | 606/230 |
| 5,522,842 A | * | 6/1996 | Shalaby | 606/230 |
| 6,462,169 B1 | * | 10/2002 | Shalaby | 528/354 |
| 2001/0051814 A1 | * | 12/2001 | Shalaby | 606/230 |

* cited by examiner

*Primary Examiner* — Corrine M McDermott
*Assistant Examiner* — Christiana Lauer
(74) *Attorney, Agent, or Firm* — McCormick, Paulding & Huber LLP

(57) ABSTRACT

Monofilament sutures are disclosed, which are formed of complaint, segmented, polyaxial, absorbable copolyesters. The sutures are capable of retaining at least 50 percent of their initial breaking strength after 6 weeks following placement in animal or human tissues.

7 Claims, No Drawings

COMPLIANT, LONG-LASTING ABSORBABLE MONOFILAMENT SUTURES

FIELD OF THE INVENTION

The present invention generally relates to compliant, absorbable monofilament sutures made of crystalline, high-lactide, segmented, polyaxial copolyesters and which retain at least 50 percent of their initial breaking strength after six weeks in the biological environment.

BACKGROUND OF THE INVENTION

Soft and pliable absorbable polymers are most often made of block or segmented copolymers consisting of soft amorphous (B) and hard crystalline (A) blocks/segments present in an A-B-A or (A-B)$_n$ arrangement. The amorphous component is usually made of flexible chains, and undergoes a glass transition below room temperature. The mobility of the polymer chains in the soft component is accordingly high, and a relatively low mechanical force is required to displace segments of the polymer chains giving rise to the soft characteristics. The crystalline hard components are made of rigid chains and contribute to the overall material physical integrity and final mechanical strength. In various soft tissue applications of sutures, they are preferred to be as soft and pliable as possible to reduce the modulus mismatch between implant and tissue, which can be traumatic and lead to increased inflammatory response. One approach towards achieving this goal is to reduce the copolymer crystallinity and the average size of individual crystallites through using tri- or tetra-functional initiators to result in polyaxial segmented chains. A second approach towards achieving a more compliant suture is to prepare a polyaxial, amorphous initiator and end-graft it with segmented crystallizable components.

Pertinent to the polyaxial approach using a polymeric initiator, U.S. Pat. No. 6,462,169 generally discloses absorbable, crystalline, monocentric, polyaxial copolymers having a crystalline component, and a flexible, amorphous component. The polymers can be prepared from a monomeric initiator, which is a tri- or tetra-functional organic compound, by reacting such initiator with at least one cyclic comonomer, selected from carbonates and lactones to form an amorphous polymeric, polyaxial initiator, and then reacting the amorphous, polymeric, polyaxial initiator with at least one lactone comprising a member selected from the group consisting of glycolide, lactide, p-dioxanone (1,4-dioxan-2-one), and combinations thereof. The copolymers are said to be crystallizable materials with melting temperatures above 100° C., which can be melt-processed into highly compliant absorbable films and fibers. Meanwhile, absorbable fibers made according to the teaching of U.S. Pat. No. 6,462,169 comprised copolymers with high-glycolide-based hard crystallizable components. This limited the respective fibers' or sutures' ability to maintain their mechanical properties in vivo beyond 4 weeks.

Following the successful introduction of polyglycolide (PG, Dexon®, U.S. Surgical Corp., Norwalk, Conn.) and 90/10 poly(glycolide-co-l-lactide (Vicryl®, Ethicon, Somerville, N.J.) as braided sutures, surgeons expressed a strong demand for absorbable, monofilament sutures with longer in vivo breaking strength retention (BSR) profiles and smoother surfaces as compared to their braided counterparts. This led to the development of poly-p-dioxanone (PDS®, Ethicon) and glycolide/trimethylene carbonate block copolymer (Maxon®, Tyco Healthcare), which exhibit BSR of 50 and 30 percent at five weeks, respectively. More recently, there has been a new demand for longer-lasting sutures, which retain more than 50 percent in vivo BSR at 6 to 12 weeks. Accordingly, a 95/5 linear l-lactide/glycolide random copolyester and segmented 88/12 l-lactide/ trimethylene carbonate copolymers were developed into Panacryl® (Ethicon) and Osteoprene® (Poly-Med, Inc., Anderson, S.C.) braided sutures, respectively, and their BSR profiles do meet the aforementioned requirements. However, there exists a strong demand for complaint, absorbable monofilament sutures having an in vivo BSR profile that exceeds that of PDS and preferably being more than 50 percent at 6 to 12 weeks and more preferably at least 50 percent at 6 weeks post-operative. The need for such sutures has become increasingly critical as the demands for repairing compromised tissues increase with the increase in the population of geriatric and diabetic patients. Other particularly important needs for long-lasting monofilament sutures are those associated with musculoskeletal tissue repair and surgical procedures on cancer patients.

The present inventors has now surprisingly found that using lactide as the dominant comonomer for end-grafting onto the amorphous core can lead to a segmented polyaxial copolyester that is well suited for conversion to compliant monofilament sutures with a breaking strength retention (BSR) profile that exceeds any monofilament suture disclosed in the prior art. The inventors were equally surprised to find that copolymerization of l-lactide with a less reactive monomer, such as caprolactone in the presence of a non-crystalline liquid or low melting (50° C. or less) polymeric polyaxial initiator, yields a crystalline, segmented polyaxial copolyester that is suitable for producing compliant monofilament sutures with prolonged in vivo BSR profile.

SUMMARY OF THE INVENTION

Accordingly, the present invention is directed to a compliant, absorbable monofilament suture having a modulus of less than about 450 Kpsi and exhibiting an in vivo breaking strength retention of at least 35 percent at six (6) weeks, wherein the suture is formed of a crystalline, segmented, polyaxial copolyester exhibiting a heat of fusion of at least about 20 J/g, wherein the copolyester is the reaction product of at least about 60 percent by weight of I-lactide and up to about 40 percent by weight of at least one further comonomer such as glycolide, ε-caprolactone, trimethylene carbonate, p-dioxanone, or 1,5-dioxepan-2-one. Preferably, the copolyester exhibits a heat of fusion of at least about 25 J/g, and the copolyester is the reaction of about at least about 65 percent by weight of l-lactide and up to about 35 percent by weight of the at least one further comonomer. Most preferably the at least one further comonomer is ε-caprolactone. It is also preferred that the suture is surface coated with a low molecular weight caprolactone/glycolide copolyester or a nitrogenous, low molecular weight ε-caprolactone/glycolide copolyester.

In one embodiment the copolyester has a non-crystallizable core derived from at least one monomer such as trimethylene carbonate, ε-caprolactone, p-dioxanone, or 1,5-dioxepan-2-one, which is polymerized in the presence of a monocentric polyfunctional initiator such as triethanolamine or trimethylolpropane, and wherein the core is end-grafted with a crystallizable polymeric component derived from at least about 65 weight percent l-lactide and up to about 35 weight percent of at least one cyclic monomer such as glycolide, ε-caprolactone, trimethylene carbonate, p-dioxanone, or 1,5-dioxepan-2-one. For such embodiment it is preferred that the non-crystalline core makes at least about 15 percent of the total mass of the copolyester and is derived from a mixture of caprolactone and trimethylene carbonate at molar ratios of from about 90/10 to about 10/90, and that the crystalline end-grafted copolyester components make up at least about 60 percent of the total mass. For this embodiment it is preferred that the suture is surface coated with a nitrogenous, low molecular weight caprolactone/glycolide copolyester.

In another embodiment the copolyester has a crystalline core having a melting temperature of less than about 50° C. and is derived from at least one monomer such as l-lactide, trimethylene carbonate, ϵ-caprolactone, p-dioxanone, or 1,5-dioxepan-2-one, which is polymerized in the presence of a polyfunctional initiator such as triethanolamine or trimethylolpropane, and wherein the core is end-grafted with a crystallizable component derived from at least about 80 weight percent l-lactide and up to about 20 weight percent of at least one cyclic monomer such as ϵ-caprolactone, glycolide or trimethylene carbonate. Most preferably the crystalline core is derived from δ-caprolactone and from about 1 to about 30 weight percent of at least one cyclic monomer such as lactide, trimethylene carbonate, p-dioxanone, or glycolide, polymerized in the presence of a stannous octanoate catalyst and a monocentric, polyfunctional alcohol such as triethanolamine and trimethylolpropane, and the core is end-grafted with a mixture of at least 90 weight percent l-lactide and up to about 10 weight percent ϵ-caprolactone. Most preferably the crystalline core makes up at least about 20 percent of the total mass of the copolyester. It is also preferred that the final suture is surface coated with a low molecular weight caprolactone/glycolide copolyester or a nitrogenous, low molecular weight caprolactone/glycolide copolyester.

DETAILED DESCRIPTION OF PREFERRED EMBODIMENTS

The present invention represents a new milestone in the development of absorbable polymers, which are particularly useful in the manufacture of wound repair devices such as surgical sutures and is expected to create a new family of novel sutures of great clinical significance as contemporary surgery continues to advance. Further, the present invention is directed to a new approach to apply two important scientific concepts to the development of a family of clinically unique sutures.

To attend to the scientific challenges associated with clinical needs mentioned above, two novel approaches were evoked in accordance with the present invention which are pertinent to the concepts of chain segmentation and polyaxial geometry to produce uniquely tailored, high l-lactide-based copolyester. One approach towards achieving this goal is to reduce the copolymer crystallinity and the size of individual crystallites through using tri-or tetra-functional initiators to yield polyaxial segmented chains. A second approach towards achieving a more compliant suture is to prepare a polyaxial, amorphous initiator and end-graft it with segmented crystallizable components.

This invention deals, in general, with complaint, absorbable, monofilament sutures having a tensile modulus of less than about 450 Kpsi and preferably less than about 400 Kpsi and their polymer precursors comprise segmented, polyaxial, copolyester chains. The sutures are capable of maintaining more than 30 percent, and preferably more than 35 percent, of their initial breaking strength at six weeks after implantation in biological animal or human tissues. The segmented, polyaxial, copolyester chains used in preparing the suture can be formed by copolymerizing a mixture of l-lactide and one or more cyclic monomer in the presence of a polyhydroxy compound having a central carbon or nitrogen as the initiator in the presence of an organometallic compound, such as stannous octanoate and following a reaction scheme of temperature and time that leads to chain segmentation and eventual crystallization. Alternatively, the polyhydroxy organic compound with a central carbon or nitrogen can be used to prepare an amorphous, liquid, or low melting crystalline polymeric initiator using one or more cyclic monomer. The resulting polymeric, polyaxial initiator can then be end-grafted at its hydroxyl terminal with a mixture of l-lactide and a small amount of one or more cyclic monomer under conditions that are conducive for chain segmentation and eventual crystallization. A specific aspect of this invention deals with a compliant, absorbable monofilament suture having a modulus of less than 400 Kpsi and exhibiting an in vivo breaking strength retention of at least 30 percent at six (6) weeks wherein the monofilament is formed of a crystalline, segmented, polyaxial copolyester exhibiting a heat of fusion of at least 25 J/g and is based on at least 65 percent of l-lactide as a comonomer with the balance being based on one or two monomer selected from the group represented by glycolide, ϵ-caprolactone, trimethylene carbonate, p-dioxanone, and 1,5-dioxepan-2-one.

A specific aspect of this invention deals with a compliant, absorbable, monofilament suture having a modulus of less than 400 Kpsi and exhibiting an in vivo breaking strength retention of at least 30 percent at six (6) weeks wherein the monofilament is formed of a polyaxial copolyester made of a non-crystalline core made of one or more selected monomer from the group represented by trimethylene carbonate, ϵ-caprolactone, p-dioxanone, and 1,5-dioxepan-2-one wherein the core is end-grafted with crystallizable copolymeric components exhibiting a heat of fusion of at least 25 J/g and is based on at least 65 percent l-lactide as a comonomer with the balance being based on one or more monomer selected from the group represented by glycolide, ϵ-caprolactone, trimethylene carbonate, p-dioxanone, and 1,5-dioxepan-2-one, wherein the non-crystalline core represents at least 15 percent of the total mass and is made from a mixture of caprolactone and trimethylene carbonate at molar ratios ranging between 90/10 to 10/90 and crystalline end-grafted copolyester components representing more than 60 percent of the total mass and is made from a mixture of l-lactide and one or more of the monomer from the group represented by glycolide, ϵ-caprolactone, trimethylene carbonate, p-dioxanone, and 1,5-dioxepan-2-one.

Another specific aspect of this invention deals with a compliant, absorbable monofilament suture comprising a crystalline, segmented, polyaxial copolyester exhibiting a heat of fusion of at least 20 J/g and comprising the reaction product of at least about 60 percent by weight of l-lactide and a maximum of about 40 percent by weight of at least one further comonomer selected from the group consisting of glycolide, ϵ-caprolactone, trimethylene carbonate, p-dioxanone, and 1,5-dioxepan-2-one, and wherein the suture has a modulus of less than about 450 Kpsi and exhibiting an in vivo breaking strength retention of at least 35 percent at six (6) weeks, wherein the copolyester molecular chains comprise a crystalline core having a melting temperature not exceeding 50° C. and derived from at least one monomer selected from the group represented by l-lactide, trimethylene carbonate, ϵ-caprolactone, p-dioxanone, and 1,5-dioxepan-2-one, polymerized in the presence of a polyfunctional initiator such as triethanolamine or trimethylolpropane and wherein the core is end-grafted with a crystallizable component derived from at least about 80 weight percent l-lactide and a maximum of 20 weight percent of at least one cyclic monomer selected from the group represented by ϵ-caprolactone, glycolide and trimethylene carbonate, and wherein the crystalline core is derived from ε-caprolactone and 1-30 weight percent of at least one cyclic monomer selected from the group consisting of a lactide, trimethylene carbonate, p-dioxanone, and glycolide, polymerized in the presence of stannous octanoate as the catalyst and a monocentric polyfunctional alcohol such as triethanolamine or trimethylolpropane as the initiator and wherein the core is end-grafted with a mixture comprising at least 90 weight percent l-lactide and a maximum of 10 weight percent ε-caprolactone, and the core of the polyaxial copolyester comprises at least about 20 percent of the total mass.

Another aspect of this invention deals with the use of a low molecular weight CL/G copolyester coating as a surface lubricant to be applied onto the suture to improve its tie-down properties. The coating polyester may be monocentric nitrogenous in nature containing a tertiary nitrogen at its center.

Further illustrations of the present invention are provided by the following examples:

EXAMPLE 1

Preparation and Characterization of Polyaxial 50/50 Caprolactone (CL)/Trimethylene Carbonate (TMC) Copolymer (PPI)

The polyaxial polymeric initiator (PPI) is prepared by reacting equal molar quantities of CL and TMC in the presence of trimethylolpropane and stannous octanoate as initiator and catalyst, respectively. The molar ratios of monomer to initiator and monomer to catalyst are calculated as 2,200 and 10,000, respectively, based on the entire monomer charge used in preparing the PPI and its end-grafted product. The experimental details used to prepare the PPI are described, in part, in Table I, as well as those reported earlier [U.S. Pat. No. 6,462,169 (2002)]. The resulting PPI is characterized for identity and composition (IR, NMR) and molecular weight (GPC in $CH_2Cl_2$).

EXAMPLE 2

End-Grafting the PPI with a Mixture of l-Lactide and ε-Caprolactone or Glycolide (G) and Characterization of Resulting Copolyester: A General Method Both L and CL or L and G are end-grafted onto PPI following the general reaction scheme and using the comonomer aliquots noted in Table I for preparing copolyesters P1 to P6. Additional details of the polymerization process are similar to those described elsewhere [U.S. Pat. No. 6,462,169 (2002)]. The resulting copolyesters are ground, dried, and then purified by distilling residual monomers at about 100° C. under reduced pressure. The purified copolyesters (P1 to P6) are characterized for identity (IR), composition (NMR), molecular weight (for $M_n$ and $M_w$ by GPC in $CH_2Cl_2$, in terms of viscosity, using inherent viscosity), thermal properties in terms of melting temperature ($T_m$) and heat-of-fusion ($\Delta H_f$) using differential scanning calorimetry (DSC).

EXAMPLE 3

Melt-Spinning, Orientation, and Evaluation of Monofilament Tensile Properties and Knot Strength: General Method Melt-spinning is conducted using a ¾-inch single screw extruder equipped with melt-pressure regulating pump. The extrudates are collected and oriented by drawing in two stages using a combination of heated shoes and Godeys. Additional details of the drawing process are noted in Table II. The drawn monofilaments are annealed at constant length at the temperatures documented in Table II. The tensile properties and knot strength of the monofilament suture candidates are determined using an MTS MiniBionix Universal Tester, Model 858.

EXAMPLE 4

Synthesis and Characterization of Nitrogenous Polyaxial Polyester Coating, P7

A low molecular weight 95/5 caprolactone/glycolide copolymer (P7) was prepared by ring-opening polymerization of a mixture of CL and G as described earlier [U.S. Pat. No. 5,773,563 (1998)] in the presence of triethanolamine and stannous octanoate as an initiator and catalyst, respectively. At the conclusion of the polymerization, residual monomer was removed by heating at 100° C. under reduced pressure. The polymer was characterized for identity (IR), composition (NMR), molecular weight (GPC), and thermal properties (DSC).

EXAMPLE 5

Synthesis and Characterization of Polyaxial Copolyester Coating, P8

The polymer was prepared and characterized under conditions similar to those described for P7 in Example 4 with the exception of replacing triethanolamine with trimethylolpropane as the initiator.

EXAMPLE 6

Surface Coating of the Monofilaments and Retesting of their Mechanical Properties: a Typical Protocol For size 2-0 monofilament sutures, a 5 percent solution of the coating polymer P7 in acetone was used following standard dipping and drying conditions. The mechanical properties of the coated sutures were retested using a MTS MiniBionix Universal Tester, Model 858.

EXAMPLE 7

One-Step Synthesis and Characterization of Polyaxial, Segmented Copolymer, P9, of 74/26 l-Lactide/Caprolactone The copolymer was prepared by copolymerizing a 74/26 (molar) mixture of l-lactide and ε-caprolactone under dry nitrogen atmosphere in the presence of triethanolamine as initiator, monomer/initiator ratio of 2,220 and stannous octanoate as a catalyst at monomer/catalyst of 10,000. After melting the comonomers and mixing with the catalyst and initiator, the temperature was raised to 140° C. and reaction was continued for 60 hours. The polymer was isolated, ground and purified by distilling the residual monomer under reduced pressure. The purified polymer was characterized as described for P1 to P6 and pertinent analytical data are shown in Table III.

EXAMPLE 8

Conversion of P9 into a Monofilament and Evaluation of its Suture Properties

The conversion of the P9 copolymer of Example 7 to a monofilament suture was conducted following the steps set forth in Example 3. The suture was coated as in Example 6 and its properties are depicted in Table III.

EXAMPLE 9

Synthesis of an 86/14 (Molar) ∈-Caprolactone/l-Lactide Copolymer as a Core Polymeric Initiator and its End-Grafting with l-Lactide to Produce a 69/31 (by Weight) Polyaxial Segmented Copolyester (SLC-1)

For an initial charge, ∈-caprolactone (1.897 moles), l-lactide (0.297 moles), trimethylolpropane ($2.92 \times 10^{-3}$ moles), and tin(II) 2-ethyl hexanoate ($2.19 \times 10^{-4}$ moles) were added to a stainless steel reactor equipped for mechanical stirring and vacuum. The contents were dried at 40° C. under vacuum for 1 hour and the pressure equilibrated with dry nitrogen. The contents were stirred to ensure complete mixing and the temperature was raised to 165° C. The reaction was allowed to continue at 165° C. until about 90% monomer conversion was achieved. For the second charge, l-lactide (3.063 moles) was added and the temperature lowered to 140° C. Upon melting of the l-lactide, the contents were stirred until complete dissolution of the polymeric initiator was apparent. Another aliquot of tin(II) 2-ethyl hexanoate ($2.50 \times 10^{-4}$ moles) was added and the temperature raised to 160° C. The contents were stirred for about 30 minutes after the temperature reached 160° C. The stirring was stopped and the temperature lowered to 140° C. Conditions were maintained for 50 hours from the time the temperature reached 140° C.

EXAMPLE 10

Synthesis of an 86/14 (Molar) ∈-Caprolactone/l-Lactide Copolymer as a Core Polymeric Initiator and its End-Grafting with 99/1 (Molar) l-Lactide/∈-Caprolactone to Produce a 69/31 (by Weight) Polyaxial Segmented Copolyester (SLC-2)

For an initial charge, ∈-caprolactone (2.132 moles), l-lactide (0.340 moles), trimethylolpropane ($3.34 \times 10^{-3}$ moles), and tin(II) 2-ethyl hexanoate ($2.50 \times 10^{-4}$ moles) were added to a stainless steel react equipped for mechanical stirring and vacuum. The contents were dried at 40° C. under vacuum for 1 hour and the pressure equilibrated with dry nitrogen. The contents were stirred to ensure complete mixing and the temperature was raised to 165° C. The reaction was allowed to continue at 165° C. until about 90% monomer conversion was achieved. For the second charge, l-lactide (3.5 moles) was added and the temperature lowered to 140° C. Upon melting of the l-lactide, the contents were stirred until complete dissolution of the polymeric initiator was apparent. A tin(II) 2-ethyl hexanoate ($2.19 \times 10^{-4}$ moles) solution in ∈-caprolactone (0.035 moles) was then added. The contents were stirred for about 20 minutes and then the temperature raised to 160° C. The reaction was allowed to continue for about 15 minutes after the temperature reached 160° C. The stirring was stopped and the temperature lowered to 140° C. Conditions were maintained for 50 hours from the time the temperature reached 140° C.

EXAMPLE 11

Synthesis of an 86/14 (Molar) ∈-Caprolactone/l-Lactide Copolymer as a Core Polymeric Initiator and its End-Grafting with 96/4 (Molar) l-Lactide/∈-Caprolactone to Produce a 69/31 (by Weight) Polyaxial Segmented Copolyester (SLC-3)

For an initial charge, ∈-caprolactone (2.022 moles), l-lactide (0.340 moles), trimethylolpropane ($3.34 \times 10^{-3}$ moles), and tin(II) 2-ethyl hexanoate ($3.50 \times 10^{-4}$ moles) were added to a stainless steel reactor equipped for mechanical stirring and vacuum. The contents were dried at 40° C. under vacuum for 1 hour and the pressure equilibrated with dry nitrogen. The contents were stirred to ensure complete mixing and the temperature was raised to 165° C. The reaction was allowed to continue at 165° C. until about 90% monomer conversion was achieved. For the second charge, l-lactide (3.5 moles) and ∈-caprolactone (0.146 moles) were added and the temperature lowered to 140° C. Upon melting of the l-lactide, the contents were stirred until complete dissolution of the polymeric initiator was apparent. The contents were stirred for about 20 minutes and then the temperature was raised to 160° C. The reaction was allowed to continue for about 15 minutes after the temperature reached 160° C. The stirring was stopped and the temperature lowered to 140° C. Conditions were maintained for 60 hours from the time the temperature reached 140° C.

EXAMPLE 12

Synthesis of an 85/15 (molar) ∈-Caprolactone/l-Lactide Copolymer as a Core Polymeric Initiator and its End-Grafting with 95/5 (molar) l-Lactide/∈-Caprolactone to Produce a 69/31 (by Weight) Polyaxial Segmented Copolyester (SLC-4)

For an initial charge, ε-caprolactone (1.983 moles), l-lactide (0.340 moles), trimethylolpropane ($3.34 \times 10^{-3}$ moles), and tin(II) 2-ethyl hexanoate ($2.50 \times 10^{-4}$ moles) were added to a stainless steel reactor equipped for mechanical stirring and vacuum. The contents were dried at 40° C. under vacuum for 1 hour and the pressure was equilibrated with dry nitrogen. The contents were stirred to ensure complete mixing and the temperature was raised to 165° C. The reaction was allowed to continue at 165° C. until about 90% monomer conversion was achieved. For the second charge, l-lactide (3.5 moles) and ∈-caprolactone (0.184 moles) were added and the temperature was lowered to 140° C. Upon melting of the l-lactide, the contents were stirred until complete dissolution of the polymeric initiator was apparent. The contents were stirred for about 20 minutes and then the temperature was raised to 160° C. The reaction was allowed to continue for about 15 minutes after the temperature reached 160° C. The stirring was stopped and the temperature was lowered to 140° C. Conditions were maintained for 50 hours from the time the temperature reached 140° C.

EXAMPLE 13

Extrusion of SLC-1 Copolyester and Properties of its Coated and Uncoated Monofilaments Upon completion of the polymerization, the polymer was removed, ground, and sieved with a 1.7 mm sieve. Polymer granules were added to a 2 L pear shaped glass flask and transferred to a rotary evaporator. Residual monomer was removed by distillation under reduced pressure at temperatures of 40° C. for 0.75 hours, 80° C for 1.5 hours, and 1 0C for 3.5 hours. The polymer was melt extruded into monofilaments, drawn/oriented 6× using two stages with a temperature range of 65-95° C. and then coated with P8 of Example 5, using the coating process of Example 6. Typical mechanical and thermal properties of coated and uncoated monofilaments are summarized in Tables 4 and 5, respectively.

TABLE I

Synthesis and Characterization of Crystalline, Segmented, Polyaxial, Absorbable Copolyesters

| Experimental Variables | Polymer Number | | | | | |
|---|---|---|---|---|---|---|
| | P1 | P2 | P3 | P4 | P5 | P6 |
| Polyaxial Polymeric Initiator (PPI) | | | | | | |
| Monomer composition 50/50, CL/TMC (molar) | ←——— All ———→ | | | | | |
| Monomer/trimethylolpropane[a] (molar) | ←——— 2,200 ———→ | | | | | |
| Monomer/stannous octanoate[a] (molar) | ←——— 10,000 ———→ | | | | | |
| Polymerization, Temp./Time, °C./hour | ←——— 160/1.5 ———→ | | | | | |
| End-grafted Copolymer | | | | | | |
| End-graft composition (molar) | | | | | | |
| l-lactide/TMC | 94/6 | 90/10 | 94/6 | — | — | — |
| l-lactide/G | — | — | — | 94/6 | 90/10 | 94/6 |
| End-graft/PPI Wt. ratio | 70/30 | 70/30 | 76/24 | 70/30 | 70/30 | 76/24 |
| Polymerization, Temp./Time, °C./hour | ←——— 140/60 ———→ | | | | | |
| Characterization & Targeted Properties | | | | | | |
| Inherent Viscosity, dL/g | 1.5 | 1.5 | 1.6 | 1.5 | 1.5 | 1.6 |
| GPC (in $CH_2Cl_2$), $M_w$, kDa | 130 | 130 | 145 | 130 | 130 | 145 |
| DSC: $T_m$, °C. | 160 | 155 | 160 | 160 | 155 | 160 |
| $\Delta H_f$ (J/g) | 30 | 30 | 35 | 30 | 30 | 35 |

[a] Based on overall monomer charge for polymeric initiator and end-grafted copolymer.

TABLE II

Conversion of Polymers P1 to P6 to Size 2-0 Monofilaments and Their Sutures Properties

| Experimental Variables | Polymer Number | | | | | |
|---|---|---|---|---|---|---|
| | P1 | P2 | P3 | P4 | P5 | P6 |
| Polymer/Monofilament Processing Main Extrusion Temperature, °C. | 210 | 200 | 210 | 210 | 200 | 200 |
| Orientation (by 2-stage drawing) | | | | | | |
| Overall Draw Ratio (2-stage) | ←——— 4-6 x ———→ | | | | | |
| Temperature Range | ←——— 75-115° C. ———→ | | | | | |
| Annealing Temperature, °C. | 85 | 80 | 85 | 90 | 85 | 85 |
| Non-sterile Monofilament Properties | | | | | | |
| Linear Strength, Kpsi | 80 | 78 | 82 | 81 | 76 | 83 |
| Modulus, Kpsi | 210 | 210 | 230 | 220 | 220 | 240 |
| Elongation, % | 50 | 60 | 40 | 62 | 61 | 45 |
| Knot Strength, N | 28 | 29 | 30 | 28 | 29 | 30 |
| Accelerated in vitro BSR @ 50° C. & pH 7.4, % @ | | | | | | |
| Day 4 | 75 | 65 | 76 | 72 | 60 | 75 |
| Day 6 | 60 | 53 | 65 | 58 | 50 | 63 |
| Day 8 | 50 | 45 | 55 | 47 | 40 | 52 |

TABLE III

Properties of Segmented, Polyaxial Copolylactide (P9) and Coated Suture Properties of Its Monofilament as a Preliminary Control Polymer Properties
Molecular Dimensions

| | |
|---|---|
| Molecular weight by GPC (in $CH_2Cl_2$), kDa: | $M_n$ = 93, $M_w$ = 154 |
| Inherent viscosity (in $CHCl_3$), dL/g | 1.55 |
| Thermal Properties (DSC) | |
| $T_m$, ° C. | 166 |
| ΔH, J/g | 38 |
| Monofilament Suture Properties | |
| Diameter, mm | 0.26 |
| Linear Tensile Strength, Kpsi | 64 |
| Tensile Modulus, Kpsi | 329 |
| Elongation, % | 83 |
| Knot Strength, N | 19 |

TABLE IV

Typical Mechanical Properties of Monofilaments of SLC-1

| | Diameter (mm) | Linear Max Load (N) | Linear Strength (kpsi) | Modulus (kpsi) | Elongation (%) | Knot Max Load (N) |
|---|---|---|---|---|---|---|
| Uncoated | 0.36 | 44.7 | 64.6 | 394 | 43 | 39.1 |
| Coated | 0.38 | 41.9 | 53.5 | 280 | 76 | 36.5 |

$^a$the monofilaments were coated with P8 of example 5 as per the coating and testing procedures as described in example 6.

TABLE V

Typical Thermal Properties of Monofilaments of SLC-1

| | $T_m$ (° C.) | Heat of Fusion (J/g) |
|---|---|---|
| Uncoated | 166 | 33 |
| Coated | 168 | 40 |

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. A compliant, absorbable monofilament suture having a modulus of less than 400 Kpsi and exhibiting an in vivo breaking strength retention of at least 35 percent at six (6) weeks comprising a crystalline, segmented, polyaxial copolyester comprising a crystalline core made by the polymerization of ε-caprolactone and l-lactide in the presence of an initiator selected from trimethylolpropane and triethanolamine, the crystalline core end-grafted with at least 90 weight percent l-lactide and up to 10 weight percent ε-caprolactone, the copolyester having a melting point below about 50° C.

2. A compliant absorbable monofilament suture as set forth in claim 1 wherein the copolyester exhibits a heat of fusion of at least about 25 J/g, the copolyester comprising in total the reaction of about at least about 65 percent by weight of l-lactide and up to about 35 percent by weight of ε-caprolactone.

3. A compliant, absorbable monofilament as set forth in claim 2 surface coated with a nitrogenous, low molecular weight ε-caprolactone/glycolide copolyester.

4. A compliant, absorbable monofilament suture as set forth in claim 1 wherein the crystalline core comprises at least about 20 percent of the total mass of the copolyester.

5. A compliant, absorbable monofilament suture having a tensile modulus of less than about 400 Kpsi and exhibiting an in vivo breaking strength retention of at least 50 percent at six (6) weeks comprising a crystalline, segmented, polyaxial end-grafted polymer comprising an amorphous non-crystalline polyaxial core made by the polymerization of ε-caprolactone and trimethylene carbonate in the presence of an initiator selected from trimethylolpropane and triethanolamine, the amorphous core end-grafted with at least 90 weight percent l-lactide and up to 10 weight percent of at least one cyclic monomer selected from ε-caprolactone and trimethylene carbonate.

6. A compliant, absorbable monofilament suture as set forth in claim 5 wherein the non-crystalline core comprises at least 15 percent of the total mass Of the copolyester, the core comprising a mixture of caprolactone and trimethylene carbonate at molar ratios of from about 90/10 to about 10/90, and wherein the crystalline end-grafted components comprise at least 60 percent of the total mass of the copolyester.

7. A compliant, absorbable monofilament suture as set forth in claim 5 surface coated with a polyaxial, nitrogenous caprolactone/glycolide copolyester.

* * * * *